United States Patent
Gattupalli et al.

(10) Patent No.: US 10,118,878 B2
(45) Date of Patent: Nov. 6, 2018

(54) PROCESS FOR INCREASING XYLENE ISOMER TO BENZENE RATIO

(71) Applicant: UOP LLC, Des Plaines, IL (US)

(72) Inventors: Rajeswar R. Gattupalli, Buffalo Grove, IL (US); Mohamed S. M. Shakur, Hoffman Estates, IL (US); Naiyl A. Rashid, Carpentersville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/668,535

(22) Filed: Aug. 3, 2017

(65) Prior Publication Data
US 2018/0079701 A1    Mar. 22, 2018

Related U.S. Application Data

(60) Provisional application No. 62/397,296, filed on Sep. 20, 2016.

(51) Int. Cl.
*C07C 15/08*    (2006.01)
*C07C 6/12*    (2006.01)
(Continued)

(52) U.S. Cl.
CPC .............. *C07C 15/08* (2013.01); *B01D 3/143* (2013.01); *C07C 5/25* (2013.01); *C07C 5/2737* (2013.01);
(Continued)

(58) Field of Classification Search
CPC ......... C07C 15/04; C07C 15/06; C07C 15/08; C07C 15/20; C07C 6/12; C07C 5/25; B01D 3/143
See application file for complete search history.

(56) References Cited

U.S. PATENT DOCUMENTS

| | | |
|---|---|---|
| 4,244,807 A | 1/1981 | Dautzenberg et al. |
| 4,975,179 A | 12/1990 | Harandi et al. |
| | (Continued) | |

FOREIGN PATENT DOCUMENTS

| | | |
|---|---|---|
| CN | 202107668 U | 1/2012 |
| CN | 101811926 B | 6/2013 |
| | (Continued) | |

OTHER PUBLICATIONS

Phillips Petroleum Co, A New Aromatics-Recovery Process Featuring Extractive Distillation, Chem Eng (N Y) V81 N.24 71 (Nov. 11, 1974), v 81, n 24, p. 71, Nov. 11, 1974; ISSN: 00092460; Chemical Week Associates.

(Continued)

*Primary Examiner* — Brian A McCaig
*Assistant Examiner* — Jason Y Chong (57) ABSTRACT

Apparatuses and processes are provided for regulating C7 and C8 feed to an aromatics complex to increase the ratio of a selected xylene isomer to benzene ratio. Reformate may be split into three cuts in a splitter column. A side cut stream comprises predominantly C7 hydrocarbons and a bottoms steam from the splitter column comprises predominantly C8+ hydrocarbons. The relative proportion of the C7 and C8+ hydrocarbon streams sent to the aromatics complex are metered to determine the resulting ratio of a selected xylene isomer to benzene produced by the aromatics complex.

20 Claims, 2 Drawing Sheets

(51) Int. Cl.
| | |
|---|---|
| *B01D 3/14* | (2006.01) |
| *C07C 5/25* | (2006.01) |
| *C07C 5/27* | (2006.01) |
| *C07C 7/04* | (2006.01) |
| *C07C 7/12* | (2006.01) |
| *C10G 7/00* | (2006.01) |
| *C10G 45/58* | (2006.01) |
| *C10G 67/04* | (2006.01) |
| *C07C 15/04* | (2006.01) |
| *C07C 15/06* | (2006.01) |
| *C07C 15/20* | (2006.01) |

(52) U.S. Cl.
CPC ............... *C07C 6/12* (2013.01); *C07C 6/126* (2013.01); *C07C 7/04* (2013.01); *C07C 7/12* (2013.01); *C10G 7/00* (2013.01); *C10G 45/58* (2013.01); *C10G 67/0409* (2013.01); *C10G 67/0445* (2013.01); *C07C 15/04* (2013.01); *C07C 15/06* (2013.01); *C07C 15/20* (2013.01)

(56) References Cited

U.S. PATENT DOCUMENTS

| | | | |
|---|---|---|---|
| 7,304,193 | B1 | 12/2007 | Frey et al. |
| 8,679,320 | B2 | 3/2014 | Serban et al. |
| 8,882,994 | B2 | 11/2014 | Moser et al. |
| 9,024,098 | B2 | 5/2015 | Moser et al. |
| 2009/0045102 | A1* | 2/2009 | Zhou .................. C10G 29/205 208/133 |
| 2015/0038755 | A1 | 2/2015 | Corradi et al. |
| 2015/0094507 | A1 | 4/2015 | Gattupalli et al. |
| 2015/0166435 | A1* | 6/2015 | Serban .................. C10G 61/04 585/321 |
| 2016/0046544 | A1 | 2/2016 | Molinier et al. |
| 2016/0185686 | A1 | 6/2016 | Molinier et al. |

FOREIGN PATENT DOCUMENTS

| | | |
|---|---|---|
| CN | 101885661 B | 9/2013 |
| CN | 102206504 B | 12/2013 |

OTHER PUBLICATIONS

Firnhaber el al., Separation processes for the recovery of pure aromatics, DGMK Tagungsbericht, n 9903, p. 73-97, 1999; ISSN: 14339013; Conference: DGMK-Conference 'The Future Role of Aromatics in Refining and Petrochemistry', Oct. 13, 1999-Oct. 15, 1999; Publisher: Deutsche Wissenschaftliche Gesellschaft fuer Erdoel, Erdgas and Kohle e.V. (DGMK).

Vybihal, C8 and C9 Aromatics From Petroleum Fractions, Chem Prumysl N.13.617 (1963) (Abstr) Petroleum (London) V27 N.5.241 (May 1964), 1963.

Lee, et. al., Application of a fully thermally coupled distillation col. For fractionation process in naphtha reforming plant, Chemical Engineering and Processing, v 43, n 4, p. 495-501, Apr. 2004; ISSN: 02552701; Publisher: Elsevier.

Lee, et. al., Two-Liquid-Phase Extractive Distillation for Aromatics Recovery, Ind. Eng. Chem. Res. (ISSN 0888-5885) V26 N.3 564-73 (Mar. 1987), v 26, n 3, p. 564-73, Mar. 1987; ISSN: 08885885; Publisher: American Chemical Society (ACS).

Mueller, Production and Separation of Aromatics by Extraction and Extractive Distillation, Assoc FR Tech Pet "Aromatics" Meet (Paris Oct. 15, 1973) Verfahrenstechnik (Mainz) V8 N.3 88-93 (Mar. 1974), Oct. 15, 1973.

Fandary et. al., Extraction of BTX from naphtha reformate using a mixer-settler cascade, Solvent Extr. Ion Exch., 7 (4) 677-703 (1989) Chem. Abstr. Abstr. No. 22713 V112 N.4, 1989 Author affiliation: Chem Eng Dep Univ Kuwait Safat Kuwait 13060.

Kato et. al., Separation of Aromatic Hydrocarbon Contained in (Catalytic) Reformate (Gasoline) and Kerosine by Liquid Membrane Permeation, J. Jpn. Pet. Inst. (ISSN 0582-4664) V30 N.1 1-6 (Jan. 1987), v 30, n 1, p. 1-6, Jan. 1987.

Gaile et. al., Combination methods for aromatic hydrocarbons separation from catalytic reformate gasoline fractions, Neftepererab. Neftekhim. (Moscow, Russ. Fed.), n 12, p. 18-21, 2003

Gaile et. al., Recovery of arenes from the reformate of gasoline fraction by combined method of extraction and azeotropic distillation, Russian Journal of Applied Chemistry, v 80, n 4, p. 600-604, Apr. 2007; ISSN: 10704272; DOI: 10.1134/S1070427207040167.

Despa et. al., Reformate Fractionation to Obtain C6-C8 Aromatic, Mine Pet Gaze 1975 V26 N.4 198-206 Chem Abstr V83-181707 in English/Rumanian, v 26, n 4, p. 198-206, 1900; ISSN: 02503115.

Wu et. al., Dynamic control of a divided-wall column used for high-purity separation of aromatic reformate, AIChE 2012—2012 AIChE Annual Meeting, Conference Proceedings, 2012, AIChE 2012—2012 AIChE Annual Meeting, Conference Proceedings; ISBN-13: 9780816910731; Conference: 2012 AIChE Annual Meeting, AIChE 2012, Oct. 28, 2012-Nov. 2, 2012.

PCT Search Report dated Dec. 28, 2017 for corresponding PCT Application No. PCT/US2017/051940.

* cited by examiner

PROCESS FOR INCREASING XYLENE ISOMER TO BENZENE RATIO

CROSS-REFERENCE TO RELATED APPLICATION

This application claims priority from Provisional Application No. 62/397,296 filed Sep. 20, 2016, the contents of which cited application are hereby incorporated by reference in its entirety.

FIELD

The present disclosure generally relates to processes for producing a selected xylene isomer, and more particularly relates to processes for achieving a desired ration of a selected xylene isomer to benzene.

BACKGROUND

Xylenes are aromatic hydrocarbons that include a benzene ring and two methyl substituents. Based on the structural position of the methyl substituents, three isomers of xylene can be formed: paraxylene, metaxylene, and orthoxylene. Paraxylene is a feedstock for terephthalic acid, which is used in the manufacture of synthetic fibers and resins. Metaxylene is used in the manufacture of certain plasticizers, azo dyes, and wood preservatives. Orthoxylene is a feedstock for phthalic anhydride, which is used in the manufacture of certain plasticizers, dyes, and pharmaceutical products.

For production of a desired xylene isomer, a mixed stream of the three xylene isomers is typically produced before the desired xylene isomer is separated. In other words, the desired xylene is not selectively produced but is selectively separated. A desired xylene isomer can be separated from mixed xylene streams by using an adsorbent selective to the desired isomer. After the desired isomer is adsorbed from the mixed xylene stream, the remaining isomers are discharged in a mixed raffinate stream. Typically, a desorbent desorbs the desired xylene isomer from the adsorbent, and the desorbent and selected xylene isomer are collected and separated by fractionation.

The market for petrochemical products dictates the ratio of a selected xylene isomer to benzene to be achieved in an aromatics complex. To achieve a desired ratio of a selected xylene isomer to benzene, particular units in the complex must be made larger and run more severely to convert the feed to products yielding the desired ratio of a selected xylene isomer to benzene resulting in large capital and operational expense.

Accordingly, it is desirable to provide processes for more easily achieving a ratio of a selected xylene isomer to benzene, particularly in an aromatics complex.

SUMMARY

Feed to an aromatics complex which may comprise reformate is split into three cuts in a splitter column. An overhead stream from the splitter column comprises predominantly comprises C7− hydrocarbons. A side cut, intermediate stream comprises predominantly C7 hydrocarbons and a bottoms steam from the splitter column comprises predominantly C8+ hydrocarbons. Control of the benzene produced in the aromatics complex may be performed by limiting the benzene, toluene and ethylbenzene entering the aromatics complex in the intermediate and bottoms streams. Hence, the relative proportion of intermediate and bottoms streams sent to the aromatics complex will determine the resulting ratio of a selected xylene isomer to benzene produced by the aromatics complex. The overhead stream and the portions of the intermediate and bottoms streams not sent to the aromatics complex may be sent to the gasoline pool or elsewhere. Consequently, the ratio of a selected xylene isomer to benzene is achieved based on the feed to the aromatics complex, rather than by severely operating the complex to dramatically change the structure of the feed, helping in the minimization of capital and operational expenditures.

BRIEF DESCRIPTION OF THE DRAWINGS

The present embodiment will hereinafter be described in conjunction with the following drawing figures, wherein like numerals denote like elements, and wherein.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The various embodiments described herein relate to apparatuses and processes for achieving a high ratio of a selected xylene isomer to benzene. Embodiments disclosed can achieve para-xylene to benzene ratios of as high as 90:10 which have heretofore not been possible. The apparatuses and processes splitting feed to an aromatics complex to provide a intermediate or a C7 stream and a bottoms or a C8+ aromatics stream and then feeding some or all of each stream to the aromatics complex and feeding the remainder of each stream not sent to the aromatics complex elsewhere, such as to a gasoline pool. By adjusting the relative proportions of each of these streams fed to the aromatics complex, the resulting ratio of a selected xylene isomer to benzene can be achieved in the aromatics complex.

Figure 1:
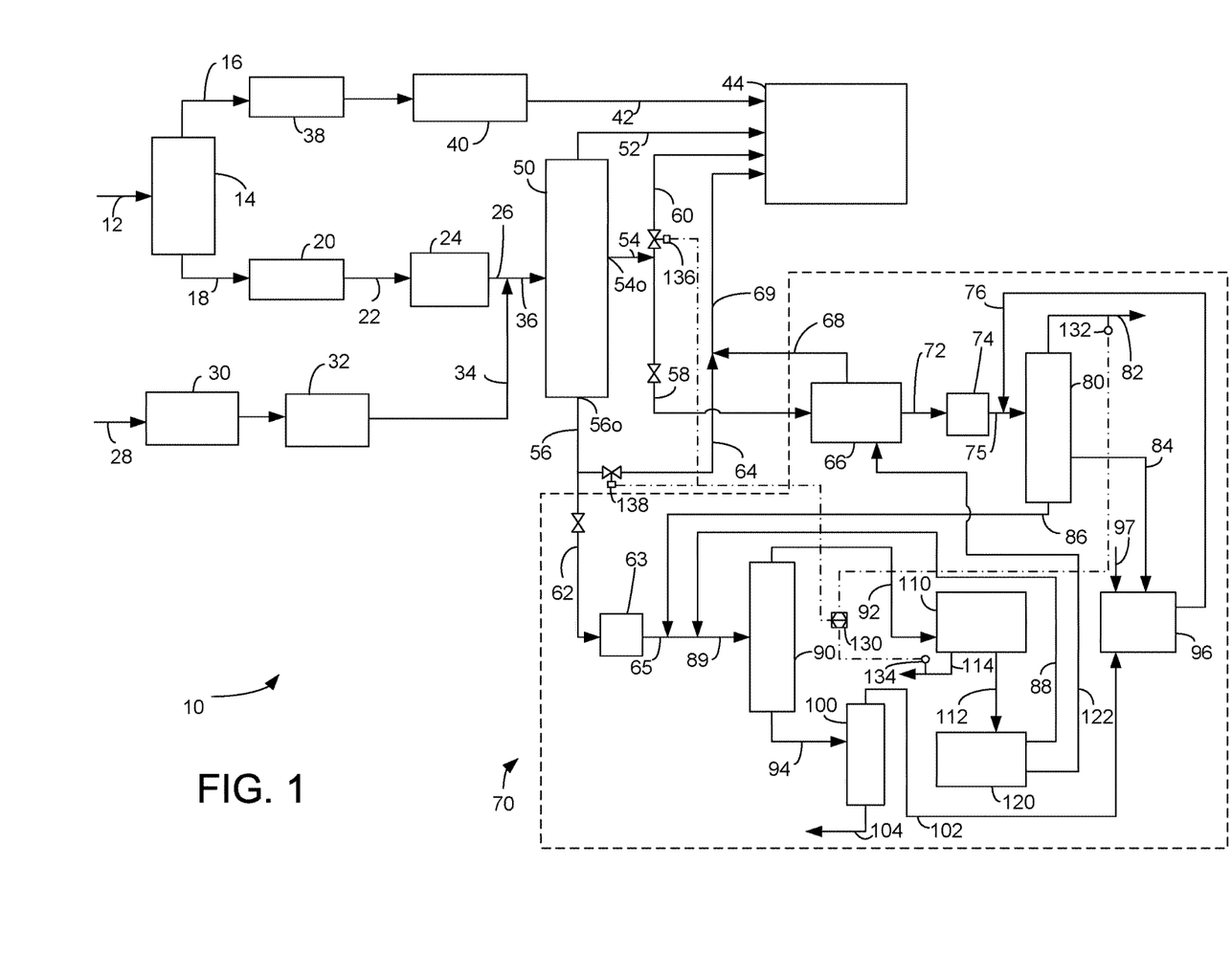
FIG. 1 is a schematic diagram of an exemplary embodiment of a process disclosed herein.

Reference is now made to an exemplary embodiment of a process and apparatus 10. A hydrocarbon stream 12 which may comprise a full range naphtha may be fed to a naphtha splitter column 14 to separate a light naphtha stream in an overhead line 16 from a heavy naphtha in a bottoms line 18. The full range naphtha may have T5 boiling point in a range of about 0° C. to about 34° C. and a T95 boiling point in a range of about 140° C. to about 215° C. The cut point between the light naphtha stream and the heavy naphtha stream in the naphtha splitter column may be between about 74° C. and about 104° C.

As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures". As used herein, the term "T5" or "T95" means the temperature at which 5 volume percent or 95 volume percent, as the case may be, respectively, of the sample boils using ASTM D-86.

The term "column" as used herein means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. Unless otherwise indicated, the top pressure is the pressure of the overhead vapor at the vapor outlet of the column, and the bottom temperature is the liquid bottom outlet temperature. Unless otherwise indicated, overhead lines and bottoms lines refer to the net lines from the column downstream of any reflux or reboil to the column. Stripping columns may omit a reboiler at a bottom of the column and instead provide heating requirements and separation impetus from a fluidized inert vaporous media such as steam.

The heavy naphtha stream in the bottoms line 18 may be hydrotreated in a heavy naphtha hydrotreating unit 20 to remove sulfur and nitrogen species as well as diolefins perhaps with sensitive noble metal catalyst systems. In an exemplary process, the heavy naphtha stream in bottoms line 18 is brought into the naphtha hydrotreating unit 20, mixed with hydrogen, and heated to a reaction temperature over a hydrotreating catalyst. Exemplary hydrotreating catalysts include metals from CAS Group VIB, VIIB, VIII, and combinations thereof. The heavy naphtha hydrotreating unit 20 may have multiple distinct stages with different catalytic zones. For example, the first stage can be operated at low temperature (e.g., about 40° C. to about 250° C.) for mainly diolefin removal, and the second stage can be operated at higher temperature (e.g., up to about 400° C.) for olefin, sulfur, and nitrogen content reduction. For a single stage, exemplary reaction temperatures are from about 250° C. to about 400° C. The main catalytic reactions in the naphtha hydrotreating unit 20 convert the contaminants of noble metal catalyst systems, such as sulfur, nitrogen, and oxygenates, via hydrogenolysis reactions to hydrogen sulfide, ammonia, and water so that they can be removed from the naphtha stream. Metals in the naphtha stream may be removed by adsorption onto the catalyst. As a result, olefins and/or diolefins are also saturated.

The resulting hydrotreated heavy naphtha stream in hydrotreated effluent line 22 contains paraffins, naphthenes and aromatics, and low levels of olefins and is fed to a reforming zone 24 for conversion of paraffins and naphthenes into aromatics. An exemplary reforming zone comprises a catalytic reformer with a continuous catalyst regenerator (CCR). The reformer may be operated at a temperature of from about 450° C. to about 560° C. A catalyst stream from the bottom of the reformer is sent to a catalyst regenerator. The regenerated catalyst is sent to the top of the reformer. Alternatively, the catalyst in the reforming zone can be regenerated in cyclic fashion by taking one of multiple reactors off-line for in situ regeneration in cyclical fashion or in semi-regenerative mode where all reactors are taken offline for in situ regeneration at one time.

Compounds in the hydrotreated heavy naphtha stream are reformed to produce a primary reformate stream in primary reformate line 26. Specifically, naphthenes are dehydrogenated to form aromatics, normal paraffins are isomerized to form isoparaffins, and paraffins are dehydrocyclized, i.e., dehydrogenated and aromatized, to form aromatics.

An optional secondary heavy naphtha stream in line 28 having a similar boiling point range as the heavy naphtha stream in the bottoms line 18 may also be hydrotreated in an optional secondary hydrotreating unit 30 and reformed in an optional secondary reforming zone 32 to provide a secondary reformate in secondary reformate line 34. The primary reformate and the optional secondary reformate may be combined in a reformate splitter feed line 36.

The light naphtha stream in the overhead line 16 may also be hydrotreated in a naphtha hydrotreater 38 to remove sulfur and nitrogen species as well as diolefins and be fed to an aliphatic isomerization unit 40. The aliphatic isomerization unit 40 isomerizes the light naphtha stream to increase the alkyl branches on the naphtha hydrocarbons and may be fed in isomerate line 42 to a gasoline pool 44 in which gasoline is stored for distribution as motor fuel.

The reformate splitter feed naphtha stream in the splitter feed line 36 preferably comprises a reformed naphtha feed stock comprising greater than about 50 wt %, suitably greater than 70 wt % or preferably greater than about 90 wt %, of aromatic hydrocarbons. The reformate splitter naphtha feed stream 36 is fed to a reformate splitter column 50. Only one naphtha feed stream need be processed and fed to the reformate splitter 50, but more naphtha feed streams may be processed and used. The reformate splitter column 50 functions to separate or "split" the naphtha stream by fractionation in the splitter feed line 36 into a lower boiling, light C7− stream which may be taken in an overhead line 52, an intermediate boiling C7 stream which may be taken from a side outlet 54o of the column, above the feed point and suitably in an upper half of the column, by an intermediate line 54 and a higher boiling, heavy C8+ aromatics stream which may be from a bottom outlet 56o of the column by a C8+ aromatics, heavy line 56. The reformate splitter may be a divided wall column with a dividing wall spaced from the top and bottom of the column or it may be two separate fractionation columns with the intermediate boiling C7 stream taken from an overhead of the second fractionation column. The reformate splitter column 50 may be configured and operated such that, for example, the overhead stream 52 may include predominantly hydrocarbons having seven or fewer carbon atoms. In an aspect, the predominant portion of C6 and C7 aliphatics fed to the reformate splitter column 50 in the reformat splitter naphtha feed stream exit in the overhead stream 52. The intermediate C7 stream should comprise no more than 10000, suitably no more than 5000 and preferably no more than 1000 wppm C8+ aromatic hydrocarbons. The intermediate stream may comprise about 1 to about 20 vol %, preferably about 2 to about 20 vol %, of the reformate splitter naphtha feed stream fed to the column in the reformate splitter feed line 36. In an aspect, at least 50 vol % and suitably at least about 75 vol % of the intermediate stream comprises toluene. The heavy C8+ aromatics stream 56 may thus comprise no more than 10000, suitably no more than 5000 and preferably no more than 1000 wppm C7− hydrocarbons. The overhead pressure in the reformate splitter column 50 is around atmospheric and the bottoms temperature is about 177 to about 204° C.

As used herein, the term "predominant", "predominantly" or "predominate" means at least 50 wt %, suitably at least 80 wt %, preferably at least 90 wt % and most preferably at least 95 wt %. The term "Cx" is to be understood to refer to molecules having the number of carbon atoms represented by the subscript "x". Similarly, the term "Cx−" refers to molecules that contain less than or equal to x and preferably x and less carbon atoms. The term "Cx+" refers to molecules with more than or equal to x and preferably x and more carbon atoms.

The intermediate C7 stream in the intermediate line 54 may be split into two streams comprising a first C7 stream, which may be a first intermediate stream, in a first intermediate line 58 taken from the intermediate C7 stream in the intermediate line 54 and an optional second C7 stream, which may be a second intermediate stream, in a second intermediate line 60 may be taken from the intermediate C7 stream in the intermediate line 54. The relative flow rates of the first C7 stream through the first intermediate line 58 and the second C7 stream through the second intermediate line 60 are regulated by control valves on each respective line. The first C7 stream in the first intermediate line 58 may comprise all or a portion of the intermediate C7 stream in the intermediate line 54, and the second C7 stream in the second intermediate line 60 may comprise all or a portion of the intermediate C7 stream in the intermediate line 54. Both of the first C7 stream in the first intermediate line 58 and the second C7 stream in the second intermediate line 60 may be aliquot portions of the intermediate C7 stream in the intermediate line 54 or the first C7 stream in the first intermediate line 58 and the second C7 stream in the second intermediate line 60 may be taken or separated from the intermediate C7 stream in the intermediate line 54 in a way that gives each stream a different composition than the other such as by fractionation.

The first C7 stream in the first intermediate line 58 taken from the C7 stream in the intermediate line 54 is fed to an aromatics complex 70 which has parameters indicated by a dotted line in FIG. 1. The second C7 stream in the second intermediate line 60 if taken from the C7 stream in the intermediate line 54 is not fed to the aromatics complex 70 but may be fed to the gasoline pool 44 or elsewhere away from the aromatics complex 70.

The heavy, C8+ aromatics stream in the heavy, C8+ aromatics line 56 may be split into two streams comprising a first C8+ aromatics stream, which may be a first heavy stream, in a first heavy, C8+ aromatics line 62 taken from the heavy, C8+ aromatics stream in the heavy, C8+ aromatics line 56 and an optional second C8+ aromatics stream, which may be a second heavy stream, in a second heavy, C8+ aromatics line 64 taken from the heavy, C8+ aromatics stream in the heavy, C8+ aromatics line 56. The relative flow rates of the first C8+ aromatics stream through the first C8+ aromatics line 62 and the second C8+ aromatics stream through the second C8+ aromatics line 64 are regulated by control valves on each respective line. The first C8+ aromatics stream in the first C8+ aromatics line 62 may comprise all or a portion of the higher boiling C8+ aromatics stream in the C8+ aromatics line 56, and the second C8+ aromatics stream in the second C8+ aromatics line 64 may comprise all or a portion of the heavy C8+ aromatics stream in the C8+ aromatics line 56. Both of the first C8+ aromatics stream in the first C8+ aromatics line 62 and the second C8+ aromatics stream in the second C8+ aromatics line 64 may be aliquot portions of the heavy, C8+ aromatics stream in the C8+ aromatics line 56 or the first C8+ aromatics stream in the first C8+ aromatics line 62 and the second C8+ aromatics stream in the second C8+ aromatics line 64 may be taken or separated from the heavy, C8+ aromatics stream in the C8+ aromatics line 56 in a way that gives each stream a different composition than the other such as by fractionation.

The first C8+ aromatics stream in the first C8+ aromatics line 62 taken from the heavy, C8+ aromatics stream in the C8+ aromatics line 56 is fed to an aromatics complex 70. The second C8+ aromatics stream in the second C8+ aromatics line 64 if taken from the heavy, C8+ aromatics stream in the C8+ aromatics line 56 may not be fed to the aromatics complex 70 but may be fed to the gasoline pool 44 for blending to make gasoline or elsewhere away from the aromatics complex 70.

At least one of the second C7 or the second intermediate stream in the second C7 or intermediate line 60 and the second C8+ aromatics or bottoms stream in the second C8+ aromatics or the second bottoms line 64 is bypassed around and not fed to the aromatics complex 70.

The flow rate of the first C7 stream in the first intermediate line 58 and the flow rate of the first C8+ aromatics stream in the first C8+ aromatics line 62 are metered in proportions to achieve a desired ratio of a selected xylene isomer to benzene in the aromatics complex 70. By regulating the flow rates of each of these streams to the aromatics complex, a surprisingly high ratio of a selected xylene isomer to benzene can be achieved. By the present process and apparatus, suitably, a mass ratio of a selected xylene isomer to benzene of at least 80:20 can be achieved; more suitably a mass ratio of a selected xylene isomer to benzene of at least 85:15 can be achieved; preferably a mass ratio of a selected xylene isomer to benzene of at least 88:12 can be achieved; and more preferably, a mass ratio of a selected xylene isomer to benzene of at least 90:10 can be achieved. The selected xylene isomer is preferably para-xylene.

The aromatics complex 70 in an embodiment may include one or more of the following units, an aromatic extraction unit 66, a first clay treater 74, a second clay treater 63, a BTX fractionation zone 80, a transalkylation unit 96, a xylene fractionation zone 90, an xylene extraction unit, a heavy aromatics column 100 and an isomerization unit 120. Additional and fewer units in the aromatics complex 70 are contemplated as well as variants of the aromatics complex 70 presented herein.

The first C7 stream in the first intermediate line 58 taken from the C7 stream is fed to an aromatics extraction unit 66 in the aromatics complex 70 to extract a C7 raffinate stream from a toluene stream. The aromatics extraction process removes non-aromatic compounds from the first C7 stream. In one particular embodiment, an extractive distillation unit may employ a sulfolane solvent to separate aromatic compounds from non-aromatic compounds. Other extraction methods, such as liquid-liquid solvent extraction are also well-known and practiced for separation of non-aromatic compounds from aromatic compounds, and their use in place of, or in addition to, extractive distillation unit is contemplated herein. The aromatics extractive unit 66 produces a C7 raffinate stream in a C7 raffinate line 68 that includes predominantly non-aromatic $C7^-$ hydrocarbons and a toluene stream 72 that includes predominantly benzene and toluene. The C7 raffinate stream in the C7 raffinate line 68 may be passed to the gasoline pool 44 perhaps via a gasoline pool line 69.

It is contemplated that the toluene stream in the toluene line 72 may be considered a C7 stream from which a first C7 or first intermediate stream is taken and fed to the aromatics complex 70 such as in line 75 and a second C7 or second intermediate stream that is not shown that is not be fed to the aromatics complex 70 such as to the gasoline pool 44 or elsewhere away from the aromatics complex 70. In such an embodiment, line 60 may be optional or dispensed.

The term, "fed to the aromatics complex" shall mean, herein, fed to a unit in the aromatics complex 70 from a unit outside of the aromatics complex or from a unit inside of the aromatics complex 70 as opposed to being fed to a unit outside of the aromatics complex 70 such as to the gasoline pool 44. The term, "fed away from the aromatics complex" shall mean herein fed to a unit or other vessel or line that is not in the aromatics complex 70.

The toluene stream in toluene line 72 may further be passed to the first clay treater 74 for increasing the purity of the aromatic compounds in such stream, for example by removing any alkylates or olefins that may be present therein. The first clay treater 74 may be configured in any known manner suitable for this purpose. The treated toluene stream leaving the first clay treater 74 in treated toluene line 75 may thus include predominantly toluene and benzene with alkylate and olefin compounds substantially, such as at least about 90 wt %, removed therefrom.

The treated toluene stream 75 may be mixed with a transalkylation effluent stream from a transalkylation effluent line 76 and be thereafter passed to a BTX fractionation zone 90. The BTX fractionation zone 80 may comprise one or more columns to provide a benzene stream in a benzene line 82, a concentrated toluene stream in a concentrated toluene line 84 and a xylene stream in a xylene line 86. The BTX fractionation zone 80 may comprise two columns with the benzene stream and the concentrated toluene stream in serial overhead lines 82 and 84, respectively, and the xylene stream in the second bottoms line. In an embodiment, the BTX fractionation zone 80 comprises a split shell distillation column 80 for the separation of the benzene stream in a benzene line 82 from the concentrated toluene stream in the concentrated toluene line 84 and the xylene stream in xylene line 86. The benzene stream, having a lower boiling point than toluene, may be removed from the distillation column 80 as an overhead product, and the toluene, having a higher boiling point than benzene, may be removed from distillation column 80 as a sidedraw product 84. Also, a net bottoms liquid stream 86 including heavier aromatic hydrocarbons such as various xylene isomers, is removed from the BTX fractionation zone 80 and thereafter fed to a xylene fractionation zone 90.

The concentrated toluene stream in the concentrated toluene line 84 may be fed to a transalkylation unit 96 to produce xylene and benzene. As shown, the transalkylation unit 96 also receives a heavy aromatics overhead stream in a heavy aromatics overhead line 102 that comprises aromatic hydrocarbons having nine or ten carbon atoms, C9-C10 aromatics, from the heavy aromatics column 100 in the aromatics complex 70.

The transalkylation unit 96 converts the toluene, C9 and C10 aromatics into benzene and xylenes in a toluene disproportionation process. Further, the transalkylation unit 96 converts a mixture of toluene and aromatic hydrocarbons having nine carbon atoms, C9, into xylenes in a transalkylation process. A hydrogen stream in line 97 may be fed to the transalkylation unit 96, so that the disproportionation and transalkylation processes are conducted in a hydrogen atmosphere to minimize coke formation. As shown, a transalkylation effluent stream in the transalkylation effluent line 76 including benzene and toluene exits the transalkylation unit 96 and may thereafter be passed to the BTX fractionation zone 80 for fractionation with the treated toluene stream in the treated toluene line 75 for the separation of toluene from the xylenes.

Turning back to the reformate splitter column 50, the first C8+ aromatics stream in the first C8+ aromatics line 62 may be passed to the second clay treater 63 for the removal of any alkylates and olefins that may be present in the first C8+ aromatics stream 62. The second clay treater 63 may be configured in any known manner suitable for this purpose as described above with regard to the first clay treater 74, thus producing a treated C8+ aromatics stream. The treated C8+ aromatics stream leaving the second clay treater 63 in a treated C8+ aromatics line may thus include predominantly C8+ aromatics with alkylate and olefin compounds substantially, such as greater than about 90 wt %, removed therefrom.

The treated C8+ aromatics stream in a treated aromatics line 65 may be combined with the xylene stream in xylene line 86 and an isomerate stream in an isomerate line 88 and be fed in a xylene feed line 89 to the xylene fractionation zone 90. The xylene fractionation zone may comprise a xylene column operated at conditions suitable for forming a concentrated xylene stream in an overhead concentrated xylene line 92. An exemplary concentrated xylene stream 92 contains predominantly and still preferably more than about 98 wt % mixed xylenes. The xylene fractionation zone 90 also produces a heavy bottom stream in a heavy bottoms line 94 perhaps from the xylene column comprising hydrocarbons having nine and more carbon atoms, C9+. An exemplary heavy bottom stream the heavy bottoms line 94 contains predominantly hydrocarbons having nine and more carbon atoms. To provide desired separation based on the relative boiling points of the compounds present, the xylene column in the xylene fractionation zone 90 may be operated from a pressure of about 5 kPa (0.7 psia) to about 1,800 kPa (260 psia) and a temperature from about 35° C. (65° F.) to about 360° C. (680° F.).

The heavy bottoms stream in the heavy bottoms line 94 containing C9+ hydrocarbons is introduced to the heavy aromatics column 100. The heavy aromatics column 100 is operated at conditions suitable for forming the heavy aromatics overhead stream in the heavy aromatics overhead line 102 comprising C9 and C10 aromatics that is fed to the transalkylation unit 96. The heavy aromatics column 100 also produces a heavy aromatics stream in a heavy aromatics bottoms line 104 that contains hydrocarbons having eleven and more carbon atoms, C11+. The heavy aromatics stream may exit the aromatics complex 70 for further processing. To provide the desired separations in the heavy aromatics fractionation column 100 based on the relative boiling points of the compounds present, the heavy aromatics column 100 can be operated from a pressure of about 5 kPa (0.7 psia) to about 1,800 kPa (260 psia) and a temperature from about 100° C. (212° F.) to about 360° C. (680° F.).

The concentrated xylene stream in the concentrated xylene line 92 is further processed to isolate a selected xylene isomer. Therefore, the concentrated xylene stream in the concentrated xylene line 92 is introduced into a xylene extraction unit 110 that extracts a selected xylene isomer from non-selected xylene isomers that comprises a xylene raffinate stream. An exemplary extraction unit 110 includes a selective adsorbent that preferentially sorbs the selected xylene isomer relative to the other xylene isomers. A desorbent is then used to desorb the selected xylene isomer from the adsorbent, and the desorbent and selected xylene isomer are collected and separated by distillation. In an exemplary embodiment, the selective adsorbent is crystalline aluminosilicate, such as type X or type Y crystalline aluminosilicate zeolites. The exemplary selective adsorbent contains exchangeable cationic sites with one or more metal cations, where the metal cations can be one or more of lithium, potassium, beryllium, magnesium, calcium, strontium, barium, nickel, copper, silver, manganese, and cadmium. Sorption conditions vary, but typically range from about 35° C. (100° F.) to about 200° C. (400° F.) and from about 100 kPa (14 psia) to about 3,500 kPa (500 psia). A selected xylene isomer stream exits the xylene extraction unit in a selected xylene isomer line 114.

Separation of the selected xylene isomer from the non-selected xylene isomers results in the formation of a xylene raffinate stream in a xylene raffinate line 112 containing the non-selected xylene isomers. In the exemplary aromatics complex 70, the xylene raffinate stream 112 is fed to an isomerization unit 120 where the non-selected xylene isomers are isomerized to produce more of the selected xylene isomer. Specifically, the removal of the selected xylene isomer in the separation unit 110 shifts the composition of the xylene raffinate stream 112 away from the equilibrium between isomer species. Because the xylene raffinate stream 112 primarily includes the non-selected two of the three xylene isomers and is relatively deficient in the selected xylene isomer, the selected xylene isomer is produced in the isomerization unit 120 to bring the xylene isomers closer to an equilibrium ratio. At about 250° C., the equilibrium ratio is about 20 to 25 wt % orthoxylene, 20 to 30 wt % paraxylene, and 50 to 60 wt % metaxylene, though the equilibrium ratio varies with temperature and other conditions.

In an exemplary embodiment, the isomerization unit 120 includes an isomerization catalyst, and operates at suitable isomerization conditions. Suitable isomerization conditions include a temperature from about 100° C. (200° F.) to about 500° C. (900° F.), or from about 200° C. (400° F.) to about 400° C. (800° F.), and a pressure from about 500 kPa (70 psia) to about 5,000 kPa (700 psia). The isomerization unit 50 includes a sufficient volume of isomerization catalyst to provide a liquid hourly space velocity, with respect to the xylene raffinate stream 112, from about 0.5 to about 50 $hf^{-1}$, or from about 0.5 to about 20 $hf^{-1}$. Hydrogen may be present at up to about 15 moles of hydrogen per mole of xylene, but in some embodiments hydrogen is essentially absent from the isomerization unit 120. The isomerization unit 120 may include one, two, or more reactors, where suitable means are employed to ensure a suitable isomerization temperature at the entrance to each reactor. The xylenes are contacted with the isomerization catalyst in any suitable manner, including upward flow, downward flow, or radial flow.

An exemplary isomerization catalyst includes a zeolitic aluminosilicate with a $Si:Al_2$ ratio greater than about 10/1, or greater than about 20/1 in some embodiments, and a pore diameter of about 5 to about 8 angstroms. Some examples of suitable zeolites include, but are not limited to, MFI, MEL, EUO, FER, MFS, MTT, MTW, TON, MOR, and FAU, and gallium may be present as a component of the crystal structure. In some embodiments, the $Si:Ga_2$ mole ratio is less than 500/1, or less than 100/1 in other embodiments. The proportion of zeolite in the catalyst is generally from about 1 wt % to about 99 wt %, or from about 25 wt % to about 75 wt %. In some embodiments, the isomerization catalyst includes about 0.01 wt % to about 2 wt % of one or more of ruthenium (Ru), rhodium (Rh), palladium (Pd), osmium (Os), iridium (Ir), and platinum (Pt), but in other embodiments the isomerization catalyst is substantially absent of any metallic compound, where substantial absence is less than about 0.01 wt %. The balance of the isomerization catalyst is an inorganic oxide binder, such as alumina, and a wide variety of catalyst shapes can be used, including spherical or cylindrical.

An isomerate stream 88 with an equilibrium distribution of xylene isomers exits the isomerization unit 120 and is recycled to the xylene fractionation zone 90. The xylenes in the isomerate stream 88 continue recycling on to the xylene extraction unit 110 in the concentrated xylene stream in the concentrated xylene line 92 from the xylene fractionation zone 90. In the exemplary apparatus 10, the isomerate stream 88 is passed through the xylene fractionation zone 90, so that C8 compounds that were changed to a compound with a larger number of carbon atoms in the isomerization unit 120 can be removed via heavy aromatics line 104. Newly generated C7− non-aromatics may be removed to the aromatics extraction unit in removal line 122 for exit from the aromatics complex in the C7 raffinate line 68. The isomerate stream 88 includes more of the selected xylene isomers than in the xylene raffinate stream 112, so more of the selected xylene isomer is available for recovery in the xylene extraction unit 110. As a result, the amount of the recovered selected xylene isomer can exceed its theoretical equilibrium value at the processing temperatures.

Separation of the selected xylene isomer from the non-selected xylene isomers in the xylene extraction unit 110 further results in the formation of an extract stream (not illustrated) containing the selected xylene isomer and the desorbent. Within the xylene extraction unit 110, the desorbent is used to desorb the selected xylene isomer from the adsorbent. The desorbent and the selected xylene isomer will comprise an extract stream, which is fed to an extract column (not shown) in the xylene extraction unit 110. The desorbent is then separated from the selected xylene isomer by fractionation in an extract column (not shown) in the xylene extraction unit 110. The selected xylene isomer exits the extract column as a bottoms stream, which, if required can be sent to a finishing column (not shown) in the xylene extraction unit 110 to further purify the selected xylene stream to meet product quality specifications. The selected xylene isomer stream leaves the finishing column as an overhead fraction and is discharged from the xylene extraction unit 110 in the selected xylene isomer line 114. The selected xylene isomer stream can be removed from the aromatics complex as the selected xylene product, e.g., a paraxylene product, an orthoxylene product, or a metaxylene product.

Several different embodiments of the xylene extraction unit 110 are possible, such as a single bed operated in batch fashion, where the xylene raffinate stream 112 is collected before the selected xylene isomer is desorbed, and the extract stream is collected after desorbing. In another embodiment, multiple adsorbent beds are used, and the introduction point of the concentrated xylene stream in the concentrated xylene line 92 and the desorbent are gradually moved through the different adsorbent beds. The discharge points of the extract stream and the xylene raffinate stream 112 are also gradually moved through the different adsorbent beds, so each individual adsorbent bed is used in a semi-batch mode and the combination simulates a continuous operation.

In a further aspect, a control scheme may be used to maintain the desired selected xylene isomer to benzene ratio in the aromatics complex 70. The desired selected xylene isomer to benzene ratio can be input as a set point in a computer 130. The computer 130 could include one or more processing devices and one or more memories for storing instructions and data used, generated, or collected by the processing device(s). The computer 130 could also include at least one network interface, such as one or more ethernet interfaces or wireless transceivers. A benzene flow rate indicator 132 in communication with the benzene line 82 may measure the flow rate of benzene in the benzene stream and sends a corresponding signal to the computer 130. Likewise, a selected xylene isomer flow rate indicator 134 in communication with the selected xylene isomer line 114 may measure the flow rate of selected xylene isomer in the selected xylene isomer stream and send a corresponding signal to the computer 130. The computer 130 receives the signals and calculates a ratio of selected xylene isomer to benzene and compares it to the set point for the selected xylene isomer to benzene ratio. If the calculated ratio is below the set point, the computer in response sends a signal to either or both of the flow rate controller 136 associated with the control valve on the second intermediate line 60 to increase the flow rate of the second C7 or intermediate stream therethrough or to the flow rate controller 138 associated with the control valve on the second C8+ aromatics or bottoms line 64 to increase the flow rate of the second C8+ aromatics stream therethrough away from the aromatics complex 70 to admit less benzene generating benzene, toluene or ethylbenzene to the aromatics complex 70. If the ratio is above the set point, the computer in response sends a signal to either or both of the flow rate controller 136 associated with the control valve on the second intermediate line 60 to decrease the flow rate of the second C7 or intermediate stream therethrough or to the flow rate controller 138 associated with the control valve on the second C8+ aromatics or bottoms line 64 to decrease the flow rate of the second C8+ aromatics stream therethrough away from the aromatics complex 70 to admit more benzene generating benzene, toluene or ethylbenzene to the aromatics complex 70. If the calculated ratio is equal to the set point, the computer need not send a signal to change a flow rate but may maintain the current signal to the flow rate controllers. Signals from the computer 130 can alternatively or additionally be sent to flow rate controllers on control valves in communication with the first intermediate line 58 or the first heavy line 62 to govern the flow rates therethrough to achieve the desired ratio.

Figure 2:
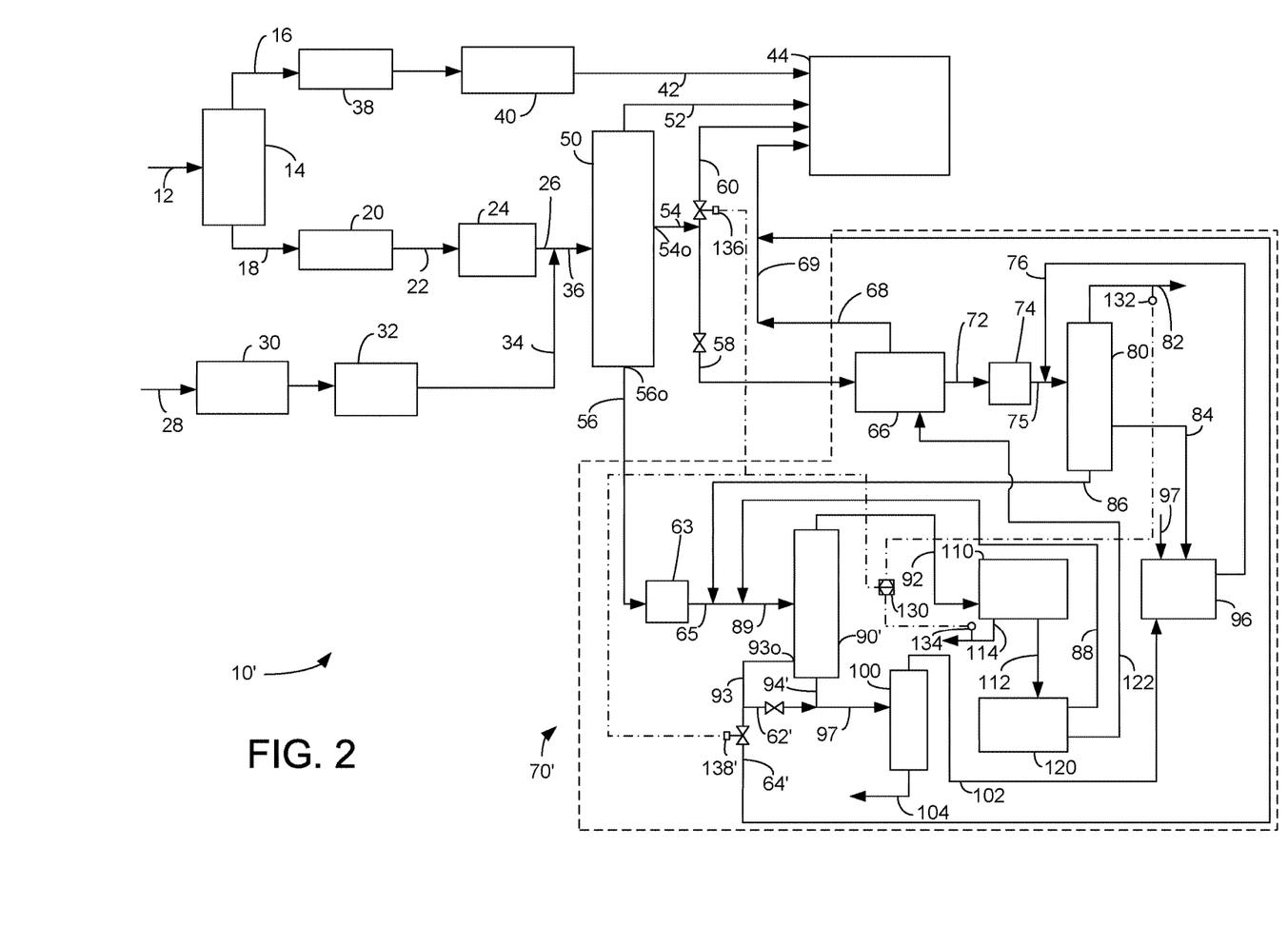
FIG. 2 is a schematic diagram of an embodiment alternate to FIG. 1.

In an embodiment of FIG. 2, a xylene fractionation zone 90' is utilized to separate a first C8+ aromatics stream from a second C8+ aromatics stream. Many of the elements in FIG. 2 have the same configuration as in FIG. 1 and bear the same reference number. Elements in FIG. 2 that correspond to elements in FIG. 1 but have a different configuration bear the same reference numeral as in FIG. 1 but are marked with a prime symbol (').

A C8+ aromatics or a heavy stream in a C8+ aromatics or a heavy line 56' may be saturated in a second clay treater 63 to provide a treated C8+ aromatics stream in a treated C8+ aromatics line 65. The treated C8+ aromatics stream in a treated aromatics line 65 may be combined with the xylene stream in xylene line 86 from the BTX fractionation zone 80 and an isomerate stream in an isomerate line 88 from the isomerization unit 120 and be fed in a xylene feed line 89 to the xylene fractionation zone 90'. The xylene fractionation zone 90' may comprise a series of columns, but in an embodiment includes a xylene column operated at conditions suitable for fractionating the C8+ aromatics stream in the C8+ aromatics line 56 to provide a first heavy stream or a first C8+ aromatics stream comprising C9 aromatics in a first C8+ aromatics or a first heavy line 62' and a second heavy stream or a second C8+ aromatics comprising C9 aromatics in a second C8+ aromatics or a second heavy line 64'.

Specifically, a concentrated xylene stream in the overhead, concentrated xylene line 92 is fed to the aromatics extraction unit 110. The xylene fractionation zone 90' also produces a C9 aromatics stream in a C9 aromatics line 93 which may be taken from a side outlet 93o from the xylene fractionation zone 90'. The xylene fractionation zone 90' also produces a heavy bottom stream in a heavy bottoms line 94' comprising hydrocarbons having 10 and more carbon atoms, C10+. The C9 aromatics stream in the C9 aromatics line 93 may be split between the first C8+ aromatics or the first heavy stream comprising C9 aromatics in the first C8+ aromatics or the first heavy line 62' which is fed to the aromatics complex 70' at a rate regulated by a control valve on the first C8+ aromatics line 62' and the second C8+ aromatics or the second heavy stream in the second C8+ aromatics or the second heavy line 64' which is not fed to the aromatics complex but perhaps to the gasoline pool 44 or elsewhere away from the aromatics complex 70 at a rate regulated by a control valve on the second C8+ aromatics line 64'. The first C8+ aromatics stream in the first C8+ aromatics line 62' reserves C9 aromatics for mixture with the heavy bottoms stream in the heavy bottoms line 94' for passage back to the aromatics complex 70' as a heavy aromatics column feed in a heavy aromatics feed line 97. Parameters of the aromatics complex 70' are indicated by a dotted line in FIG. 2.

In this embodiment, the second C7 or the second intermediate stream is not necessary in that all of the C7 or the intermediate stream may be fed to the aromatics complex 70' in the second C7 or the second intermediate line 58. The relative ratio of the selected xylene isomer to benzene is achieved by regulating the flow rate of C9 aromatics to the aromatics complex 70'

The flow rate of the first C7 stream in the first intermediate line 58 and the flow rate of the first C8+ aromatics stream in the first C8+ aromatics line 62' in addition to the C8 aromatics in the concentrated xylene stream 92 are metered in proportions to achieve a desired ratio of a selected xylene isomer to benzene in the aromatics complex 70'. By regulating the flow rates of each of these streams to the aromatics complex, a surprisingly high ratio of a selected xylene isomer to benzene can be achieved.

The flow rate controller 138' in communication with the second C8+ aromatics or the second heavy stream in the second C8+ aromatics or the second heavy line 64' receives a signal from the computer 130 to regulate the flow rate thereof away from the aromatics complex 70' at a rate regulated by a control valve on the second C8+ aromatics line 64'.

The rest of the description for the embodiment of FIG. 2 is the same as described for FIG. 1 except the control scheme is not shown in FIG. 2.

Specific Embodiments

While the following is described in conjunction with specific embodiments, it will be understood that this description is intended to illustrate and not limit the scope of the preceding description and the appended claims.

A first embodiment of the invention is a process for preparing a feed for an aromatics complex comprising fractionating a naphtha stream to provide a C7 stream and a C8+ aromatics stream; feeding a first C7 stream taken from the C7 stream to the aromatics complex; feeding a first C8+ aromatics stream taken from the C8+ aromatics stream to the aromatics complex; and feeding a second C7 stream taken from the C7 stream away from the aromatics complex; or feeding a second C8+ aromatics stream taken from the C8+ aromatics stream away from the aromatics complex. An embodiment of the invention is one, any or all of prior embodiments in this paragraph up through the first embodiment in this paragraph comprising feeding the first C7 stream taken from the C7 stream to an aromatics extraction unit in the aromatics complex to extract a C7 raffinate stream from a toluene stream. An embodiment of the invention is one, any or all of prior embodiments in this paragraph up through the first embodiment in this paragraph comprising feeding the C7 raffinate stream to a gasoline pool. An embodiment of the invention is one, any or all of prior embodiments in this paragraph up through the first embodiment in this paragraph comprising calculating a selected xylene isomer to benzene ratio and changing a flow rate of the second C7 stream and/or the second C8+ aromatics stream in response to the calculated selected xylene isomer to benzene ratio. An embodiment of the invention is one, any or all of prior embodiments in this paragraph up through the first embodiment in this paragraph comprising fractionating the C8+ aromatics stream to provide the first stream of the C8+ aromatics stream comprising C8 aromatics and the second stream of the C8+ aromatics stream comprising C9 aromatics. An embodiment of the invention is one, any or all of prior embodiments in this paragraph up through the first embodiment in this paragraph comprising fractionating the toluene stream to separate a benzene stream from a concentrated toluene stream. An embodiment of the invention is one, any or all of prior embodiments in this paragraph up through the first embodiment in this paragraph comprising feeding the concentrated toluene stream to a transalkylation unit to produce xylene and benzene. An embodiment of the invention is one, any or all of prior embodiments in this paragraph up through the first embodiment in this paragraph further comprising fractionating a transalkylation effluent with the toluene stream. An embodiment of the invention is one, any or all of prior embodiments in this paragraph up through the first embodiment in this paragraph comprising separating a xylene stream from the benzene stream and the concentrated toluene stream and feeding the xylene stream to a xylene column in the aromatics complex to separate a concentrated xylene stream. An embodiment of the invention is one, any or all of prior embodiments in this paragraph up through the first embodiment in this paragraph comprising feeding the concentrated xylene stream to a xylene extraction unit to extract a selected xylene isomer stream from a xylene raffinate stream. An embodiment of the invention is one, any or all of prior embodiments in this paragraph up through the first embodiment in this paragraph comprising isomerizing the xylene raffinate stream in an isomerization unit to produce more selected xylene isomers and recycling an isomerate stream to the xylene extraction unit via the xylene column. An embodiment of the invention is one, any or all of prior embodiments in this paragraph up through the first embodiment in this paragraph comprising producing a mass ratio of paraxylene to benzene of at least 85:15.

A second embodiment of the invention is a process for producing aromatics comprising fractionating a naphtha stream to provide an intermediate stream and a heavy stream; feeding a first intermediate stream taken from the intermediate stream to an aromatics extraction unit to extract a raffinate stream from a toluene stream; feeding all or a first portion of the heavy stream to a xylene column; and feeding a second intermediate stream taken from the intermediate stream to a gasoline pool; or feeding all or a second portion of the heavy stream to a the gasoline pool. An embodiment of the invention is one, any or all of prior embodiments in this paragraph up through the second embodiment in this paragraph comprising feeding the raffinate stream to the gasoline pool. An embodiment of the invention is one, any or all of prior embodiments in this paragraph up through the second embodiment in this paragraph comprising feeding a second portion of the heavy stream to the gasoline pool. An embodiment of the invention is one, any or all of prior embodiments in this paragraph up through the second embodiment in this paragraph comprising fractionating the heavy stream to provide the first portion of the heavy stream comprising C8 aromatics and a second portion of the heavy stream comprising C9 aromatics. An embodiment of the invention is one, any or all of prior embodiments in this paragraph up through the second embodiment in this paragraph comprising feeding the toluene stream to a benzene column to separate a benzene stream from a concentrated toluene stream and a xylene stream; feeding the concentrated toluene stream to a transalkylation reactor to produce xylene and benzene and passing the xylene stream to a xylene column to produce a concentrated xylene stream to an xylene extraction unit.

A third embodiment of the invention is a process for producing aromatics comprising fractionating a naphtha stream to provide a C7 stream and a C8+ aromatics stream; feeding a first C7 stream taken from the C7 stream to an aromatics complex; feeding a second C7 stream taken from the C7 stream to a gasoline pool; feeding a first C8+ aromatics stream taken from the C8+ aromatics stream to an aromatics complex; and feeding a second C8+ aromatics stream taken from the C8+ aromatics stream to the gasoline pool. An embodiment of the invention is one, any or all of prior embodiments in this paragraph up through the third embodiment in this paragraph comprising feeding the first C7 stream to an aromatics extraction unit in the aromatics complex to extract a C7 raffinate stream from a toluene stream and passing the C7 raffinate stream to the gasoline pool. An embodiment of the invention is one, any or all of prior embodiments in this paragraph up through the third embodiment in this paragraph comprising fractionating the C8+ aromatics stream to provide the first C8+ aromatics stream taken from the C8+ aromatics stream comprising C8 aromatics and a second C8+ aromatics stream taken from the C8+ aromatics stream comprising C9 aromatics.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:
1. A process for producing aromatics in an aromatics complex comprising:
fractionating a naphtha stream to provide a C7 stream and a C8+ aromatics stream;
feeding a first C7 stream taken from the C7 stream to the aromatics complex comprising an aromatics extraction unit, a BTX fractionation zone, a xylene fractionation zone, and a transalkylation unit and/or an isomerization unit;
feeding a first C8+ aromatics stream taken from the C8+ aromatics stream to the aromatics complex; and
feeding a second C7 stream taken from the C7 stream away from the aromatics complex; or
feeding a second C8+ aromatics stream taken from the C8+ aromatics stream away from the aromatics complex.
2. The process of claim 1 comprising feeding the first C7 stream taken from the C7 stream to the aromatics extraction unit in the aromatics complex to extract a non-aromatic C7 raffinate stream from a toluene stream.

3. The process of claim 2 comprising feeding the C7 raffinate stream to a gasoline pool.

4. The process of claim 2 comprising fractionating the toluene stream to separate a benzene stream from a concentrated toluene stream.

5. The process of claim 4 comprising feeding the concentrated toluene stream to the transalkylation unit to produce xylene and benzene.

6. The process of claim 5 further comprising fractionating a transalkylation effluent with the toluene stream to obtain a xylene stream in addition to the benzene stream and the concentrated toluene stream.

7. The process of claim 6 comprising feeding the xylene stream to the xylene fractionation zone in the aromatics complex to separate a concentrated xylene stream.

8. The process of claim 7 comprising feeding the concentrated xylene stream to a xylene extraction unit to extract a selected xylene isomer stream from a xylene raffinate stream.

9. The process of claim 8 comprising isomerizing the xylene raffinate stream in the isomerization unit to produce more selected xylene isomer and recycling an isomerate stream to said xylene extraction unit via said xylene fractionation zone.

10. The process of claim 1 comprising calculating a selected xylene isomer product to benzene product ratio and changing a flow rate of the second C7 stream and/or the second C8+ aromatics stream in response to the calculated selected xylene isomer product to benzene product ratio.

11. The process of claim 10 comprising fractionating said C8+ aromatics stream to provide said first C8+ aromatics stream comprising C8 aromatics and said second C8+ aromatics stream comprising C9 aromatics.

12. The process of claim 1 comprising recovering paraxylene and benzene from the aromatics complex at a mass ratio of paraxylene to benzene of at least 85:15.

13. A process for producing aromatics in an aromatics complex comprising an aromatics extraction unit, a BTX fractionation zone, a xylene fractionation zone, and a transalkylation unit and/or an isomerization unit, the process comprising the steps of:
   fractionating a naphtha stream to provide an intermediate stream and a heavy stream;
   feeding a first intermediate stream taken from the intermediate stream to an aromatics extraction unit to extract a raffinate stream from a toluene stream;
   feeding all or a first portion of the heavy stream to a xylene column; and
   feeding a second intermediate stream taken from the intermediate stream to a gasoline pool; or
   feeding a second portion of the heavy stream to a the gasoline pool.

14. The process of claim 13 comprising feeding the raffinate stream to the gasoline pool.

15. The process of claim 13 comprising feeding the second portion of the heavy stream to the gasoline pool.

16. The process of claim 15 comprising fractionating said heavy stream to provide said first portion of the heavy stream comprising C8 aromatics and a second portion of the heavy stream comprising C9 aromatics.

17. The process of claim 13 comprising feeding the toluene stream to a BTX fractionation zone to separate a benzene stream from a concentrated toluene stream and a xylene stream; feeding the concentrated toluene stream to a transalkylation unit to produce xylene and benzene; passing the xylene stream to a xylene fractionation zone to produce a concentrated xylene stream; and passing the concentrated xylene stream to an xylene extraction unit to extract a selected xylene isomer.

18. A process for producing aromatics comprising:
   fractionating a naphtha stream to provide a C7 stream and a C8+ aromatics stream;
   feeding a first C7 stream taken from the C7 stream to an aromatics complex comprising an aromatics extraction unit, a BTX fractionation zone, a xylene fractionation zone, and a transalkylation unit and/or an isomerization unit;
   feeding a second C7 stream taken from the C7 stream to a gasoline pool;
   feeding a first C8+ aromatics stream taken from the C8+ aromatics stream to the aromatics complex; and
   feeding a second C8+ aromatics stream taken from the C8+ aromatics stream to the gasoline pool.

19. The process of claim 18 comprising feeding the first C7 stream to the aromatics extraction unit in said aromatics complex to extract a C7 raffinate stream from a toluene stream and passing said C7 raffinate stream to the gasoline pool.

20. The process of claim 18 comprising fractionating said C8+ aromatics stream to provide said first C8+ aromatics stream taken from the C8+ aromatics stream comprising C8 aromatics and a second C8+ aromatics stream taken from the C8+ aromatics stream comprising C9 aromatics.

* * * * *